United States Patent
Momiuchi et al.

(10) Patent No.: US 6,908,461 B2
(45) Date of Patent: Jun. 21, 2005

(54) LASER DEVICE FOR MEDICAL TREATMENT SYSTEM

(75) Inventors: Masayuki Momiuchi, Tokyo-to (JP); Taizo Eno, Tokyo-to (JP); Yoshiaki Goto, Tokyo-to (JP); Hideo Sagehashi, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 10/725,757

(22) Filed: Dec. 2, 2003

(65) Prior Publication Data

US 2004/0133191 A1 Jul. 8, 2004

(30) Foreign Application Priority Data

Dec. 27, 2002 (JP) .......................... 2002-381326

(51) Int. Cl.⁷ ............................................. A61B 18/18
(52) U.S. Cl. ............................. 606/10; 606/16; 606/18; 398/43; 398/48; 398/82; 398/91; 219/121.6; 219/121.76

(58) Field of Search .......................... 606/2, 10, 16–18; 398/43–51, 82–88, 91–95, 101; 219/121.6, 121.74–121.76; 359/33; 430/945

(56) References Cited

U.S. PATENT DOCUMENTS

| | | | | |
|---|---|---|---|---|
| 4,579,430 A | * | 4/1986 | Bille | 351/206 |
| 4,854,320 A | * | 8/1989 | Dew et al. | 606/3 |
| 4,881,808 A | * | 11/1989 | Bille et al. | 351/221 |
| 4,994,059 A | * | 2/1991 | Kosa et al. | 606/12 |
| 5,350,375 A | * | 9/1994 | Deckelbaum et al. | 606/7 |
| 5,549,596 A | * | 8/1996 | Latina | 606/4 |
| 5,997,141 A | * | 12/1999 | Heacock | 351/221 |
| 6,110,165 A | * | 8/2000 | Ota | 606/4 |
| 6,626,900 B1 | * | 9/2003 | Sinofsky et al. | 606/15 |

* cited by examiner

Primary Examiner—A. Farah
(74) Attorney, Agent, or Firm—Nields & Lemack

(57) ABSTRACT

A laser device for medical treatment system, comprising at least a plurality of laser beam emitting sources, a laser beam multiplexing means for superimposing the laser beams emitted from the laser beam emitting sources, and a beam mixing means where the laser beams from the laser beam multiplexing means enter.

6 Claims, 4 Drawing Sheets

LASER DEVICE FOR MEDICAL TREATMENT SYSTEM

BACKGROUND OF THE INVENTION

The present invention relates to a laser device for emitting a plurality of laser beams, which are coaxially superimposed on each other.

A medical treatment system using a laser beam is now widely known. By irradiating laser beams, the system is used for performing photocoagulation, resection, incision, etc. of an affected site of a patient on non-contact basis. Color of each of the laser beams, i.e. a wavelength of the laser beam used in the device differs according to the type of medical treatment. For a laser device for emitting a laser beam to be used in a medical treatment system, it is desirable that laser beams with a plurality of wavelengths can be sent to the medical treatment system.

As a laser device for emitting laser beams with a plurality of wavelengths, a device shown in FIG. 5 has been known in the past. A medical treatment system (a slit lamp) 19 using the laser device is shown in FIG. 6.

FIG. 5 represents general concept of a laser device. In the figure, reference numeral 1 denotes a laser device, and 2 denotes an optical fiber for propagation to guide the laser beams from the laser device 1 toward the medical treatment system 19. An output unit of the laser device 1 is connected with the optical fiber 2 for propagation via an optical connector 3 so that it can be attached to or removed from the optical fiber.

As laser beam emitting sources, a laser beam light source unit 10 comprises a first laser oscillator 4 for emitting a laser beam 7 with a wavelength of $\lambda1$, a second laser oscillator 5 for emitting a laser beam 8 with a wavelength of $\lambda2$, and a third laser oscillator 6 for emitting a laser beam 9 with a wavelength of $\lambda3$. The laser beams 7, 8 and 9 emitted respectively from the first laser oscillator 4, the second laser oscillator 5, and the third laser oscillator 6 are superimposed on each other on a same axis via a beam multiplexer 11.

The beam multiplexer 11 comprises a first multiplexer 12 and a second multiplexer 13 arranged on an optical axis of the laser beam 7. It has a deflection mirror 14 on an optical axis of the laser beam 8 and has a deflection mirror 15 on an optical axis of the laser beam 9. The first multiplexer 12 allows the laser beam 7 with the wavelength of $\lambda1$ to pass, while the first multiplexer 12 reflects the laser beam 8 with the wavelength of $\lambda2$. The second multiplexer 13 allows the laser beams 7 and 8 to pass, while the second multiplexer 13 reflects the laser beam 9 with the wavelength of $\lambda3$.

The laser beam 7 emitted from the first laser oscillator 4 passes through the first multiplexer 12 and the second multiplexer 13 and enters a condenser lens 17. The laser beam 8 is reflected by the deflection mirror 14 and the first multiplexer 12. After being superimposed on the same optical axis as the laser beam 7, the laser beam 8 passes through the second multiplexer 13 and enters the condenser lens 17. The laser beam 9 is reflected by the deflection mirror 15 and the second multiplexer 13. The laser beam 9 is then superimposed on the same optical axis as the laser beams 7 and 8 and enters the condenser lens 17 as a coaxial multi-laser beam 16. The condenser lens 17 converges the coaxial multi-laser beam 16 and allows the laser beam to enter the optical fiber 2 for propagation via the optical connector 3. The optical fiber 2 for propagation guides the coaxial multi-laser beams 16 toward a medical treatment system such as a photocoagulator, a slit lamp, etc.

In the conventional type laser device as described above, it is difficult that optical axes of the laser beams 7, 8 and 9 perfectly concur with each other. Further, the laser beams 7, 8 and 9 do not necessarily have the same numerical aperture (NA). When the laser beams 7, 8 and 9 converged by the condenser 17 have different numerical apertures, it is difficult that all of the laser beams 7, 8 and 9 enter the optical fiber 2 for propagation without optical loss when the laser device 1 and the optical fiber 2 are connected via the optical connector 3. It is also difficult that these laser beams enter the optical fiber 2 for propagation under the completely same condition without causing the deviation of the optical axis.

For this reason, when the laser beams are projected to the site to be treated of a patient, troubles often occur such as the development of speckles in light intensity distribution at an irradiating point.

SUMMARY OF THE INVENTION

It is an object of the present invention to provide a laser device for emitting a plurality of laser beams by superimposing on a same optical axis, which makes it possible to superimpose the laser beams in such an extent as to cause practically no trouble and to avoid the development of speckles in light intensity distribution at an irradiating point.

To attain the above object, the present invention provides a laser device for medical treatment system, which comprises at least a plurality of laser beam emitting sources, a laser beam multiplexing means for superimposing the laser beams emitted from the laser beam emitting sources, and a beam mixing means where the laser beams from the laser beam multiplexing means enter. Also, the present invention provides the laser device for medical treatment system as described above, wherein the beam mixing means is an optical fiber. Further, the present invention provides the laser device for medical treatment system as described above, wherein the beam mixing means is an optical waveguide. Also, the present invention provides the laser device for medical treatment system as described above, wherein the plurality of laser beams have different wavelengths and wherein the beam multiplexer comprises an optical member which transmits the laser beams by selecting the wavelength and which reflects the laser beam with a wavelength other than transmission wavelength. Further, the present invention provides the laser device for medical treatment system as described above, wherein the plurality of laser beams have different directions of polarization and wherein the beam multiplexing means has a polarizing plate. Also, the present invention provides the laser device for medical treatment system as described above, wherein the plurality of laser beams is entered to the beam multiplexing means and wherein the beam multiplexing means comprises a condenser lens which has an optical axis in parallel to the plurality of laser beams. Further, the present invention provides the laser device for medical treatment system as described above, wherein the beam multiplexing means has a plurality of optical fibers where the laser beams enter individually, and the optical fibers have output ends integrated by being welded and deposited. Also, the present invention provides the laser device for medical treatment system as described above, wherein there is provided a photodetector for detecting a reflection light at an incident end of the beam mixing means, and the photodetector controls emission of the laser beams from the laser beam emitting sources based on the result of detection. Further, the present invention provides the laser device for medical treatment system as described above, wherein the device comprises the laser beam emitting sources, the laser beam multiplexing means, and the beam mixing means integrated with each other, and the device can be attached to or removed from a medical treatment system via an optical connector.

DETAILED DESCRIPTION OF THE PREFERRED EMBODIMENTS

Figure 1:
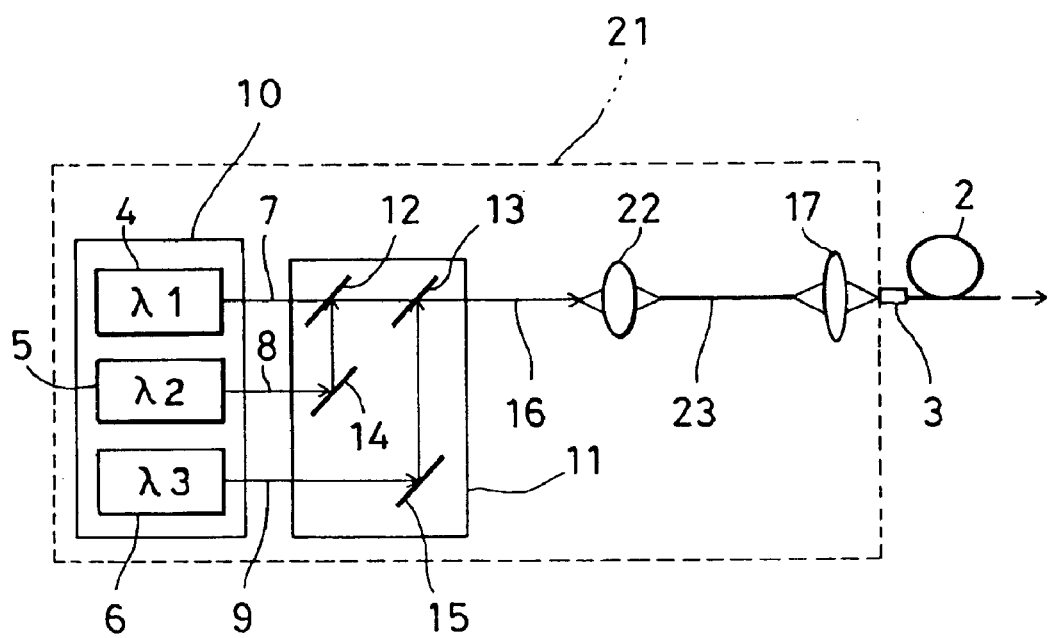
FIG. 1 is a schematical block diagram showing an embodiment of the present invention.

Description will be given below on embodiments of the present invention referring to the drawings.

Figure 5:
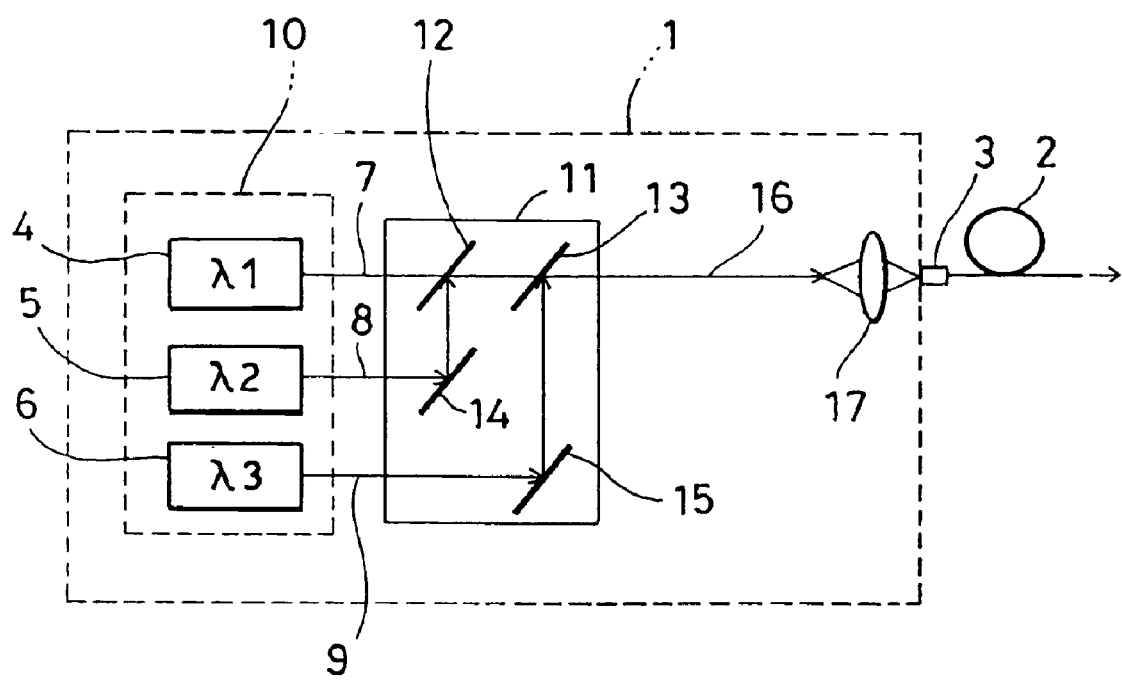
FIG. 5 is a schematical block diagram showing a conventional example.
Figure 6:
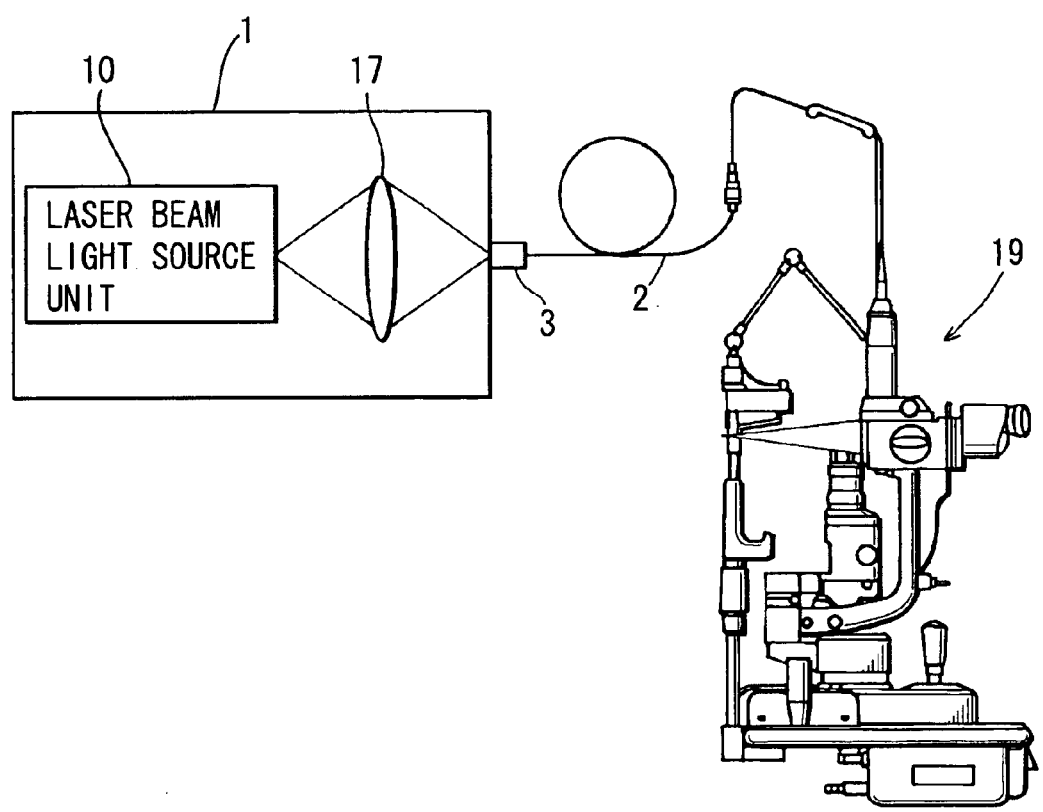
FIG. 6 is a schematical drawing of a medical treatment system.

In FIG. 1, the same component as shown in FIG. 5 is referred by the same symbol, and detailed description is not given here.

A laser device 21 comprises a laser light source unit 10, which consists of a first laser oscillator 4, a second laser oscillator 5, and a third laser oscillator 6, serving as laser emitting sources for emitting a plurality of laser beams, a beam multiplexer 11 for superimposing coaxial multi-laser beams 16 emitted from the first laser oscillator 4, the second laser oscillator 5, and the third laser oscillator 6 onto a same optical axis, and a condenser lens 17 for projecting a laser beam from the laser device 21.

Further, the laser device 21 comprises a second condenser lens 22 and a beam mixing optical fiber 23 on the optical axis of the coaxial multi-laser beams 16 emitted from the beam multiplexer 11. The coaxial multi-laser beams 16 emitted from the beam multiplexer 11 are converged to an end surface of the condenser lens 17. The laser beams emitted from the laser device 21 are converged to an incident end of an optical connector 3 via the condenser lens 17. The laser device 21 is designed in an integrated construction, and the laser device 21 can be attached to or removed from the optical fiber 2 for propagation via the optical connector 3.

The beam mixing optical fiber 23 reflects the incident laser beams in it by multiple reflection. Diverse propagation modes are excited, interference between propagation modes is suppressed, and light intensity distribution of the emitted laser beams is resolved. Multiple reflection of the laser beams inside the beam mixing optical fiber 23 makes it possible to eliminate the influence from difference of incident angles to the beam mixing optical fiber 23. As the laser beams emitted from the beam mixing optical fiber 23, the laser beams 7, 8 and 9 are completely superimposed on the same optical axis.

In order that the beam mixing optical fiber 23 effectively reflects the incident laser beams by multiple reflection, the beam mixing optical fiber 23 is designed in form of a coil, or a core diameter of the beam mixing optical fiber 23 is reduced, or the core diameter is reduced and the optical fiber is designed in form of a coil. If optical loss between the beam mixing optical fiber 23 and the optical connector 3 is taken into account, it is designed in such manner that a product K1 (i.e. a product of numerical aperture NA1 of the beam mixing optical fiber 23 and the core diameter D1) has a relation of K1≦K2 with respect to a product K2 (i.e. a product of numerical aperture NA2 of the optical fiber 2 for propagation and the core diameter D2).

As a parameter to express quality of the laser beam, $M^2$ is known. The specification of the optical members to constitute the laser device 21 is determined so that the parameter $M^2$ of beam quality of the laser beam emitted from the laser device 21 will be in the relation of: $10 \leq M^2 \leq 22$.

The parameter $M^2$ is defined as follows:

$$W = M\omega$$

$$\Theta = M\theta$$

$$\theta = \lambda/(\pi\omega)$$

$$W \cdot \Theta = M^2(\omega \cdot \theta)$$

$$= M^2 \lambda / \pi$$

where the symbol W represents a beam waist, and $\Theta$ stands for a spreading angle.

Here, the symbol $\lambda$ denotes a wavelength of the laser beam, and $\omega$ and $\theta$ represent respectively a beam waist and a spreading angle of a fundamental mode (Gauss beam) in the wavelength $\lambda$ of the laser beam. The deviation of the laser beam from the fundamental mode is represented by $M^2(M)$.

In general, a beam product ($W \cdot \Theta$) is turned to a conservative quantity under a lens optical system, and it is not preserved in a laser beam, which enters the optical fiber 2 for propagation in multiple mode. Depending on a length of the optical fiber 2 for propagation and on a curvature of a loop portion of the optical fiber 2 for propagation, the beam quality is deteriorated down to a value (D2·NA2/2), which is determined by fiber characteristics. D2 represents a core diameter of the optical fiber 2 for propagation.

A laser beam propagating in the optical fiber 2 for propagation can be defined in similar manner. If it is supposed that a diameter of the converged beam to the optical fiber 2 for propagation (core diameter D2; numerical aperture NA2) is $\phi$ and incident NA is $NA_i$, the following equation can be obtained under a connecting condition ($\phi \leq D2$ and $NA_i \leq NA2$) to the optical fiber 2 for propagation:

$$W \cdot \Theta = M^2 \lambda / \pi$$

$$= D \cdot NA_i / 2$$

$$\leq D2 \cdot NA_e / 2$$

($NA_i \leq NA_e \leq NA_f$ (numerical aperture of the optical fiber for propagation))

where $NA_e$ is an exit NA from the optical fiber 2 for propagation.

Then, the following equation can be established:

$$M^2 \leq (\pi D2 / 2\lambda) \cdot NA_e$$

In case a parameter $M^2$ of the beam quality of the laser beam emitted from the laser device 21 is within a range of $8 \leq M^2 \leq 22$, an optical fiber with common core diameters D50μm (NA=0.12) or D75μm (NA=0.12) can be used as the optical fiber 2 for propagation in order to propagate to a slit lamp 19. In case the former optical fiber for propagation is used, overall propagation efficiency of 50% or more can be expected within a range of $0.06 \leq NA_e \leq NA2$ from $8 \leq (\pi\phi/2\lambda) \cdot NA_e \leq 22$.

Also, in case the latter optical fiber for propagation is used, overall propagation efficiency of 50% or more can be expected within a range of $0.06 \leq NA_e \leq 0.1$ in the same manner. Of course, cross-sectional light intensity distribution is uniform within this range. If fiber specification is different, the exit allowable range of the optical fiber is different, but the allowable range of beam characteristics of the laser beam is not changed.

The laser beam multiplexed by the beam multiplexer 11 may be under the conditions of $\lambda 1 > \lambda 2 > \lambda 3$ or $\lambda 1 < \lambda 2 < \lambda 3$. Or, a laser beam with different direction of polarization may be used and polarizing mirrors may be used as the first beam multiplexer 12 and the second beam multiplexer 13. Or, the first beam multiplexer 12 and the second beam multiplexer 13 . . . may be designed in such manner that wavelengths and directions of polarization of the laser beams are combined together so as to transmit or reflect by selecting the wavelength. Or, the first beam multiplexer 12 and the second beam multiplexer 13 . . . may be designed in such manner that polarizing plates are combined.

When medical treatment is carried out with the above embodiment, the first laser oscillator 4, the second laser oscillator 5 and the third laser oscillator 6 are selected and driven, and the wavelength is selected depending on the details of the treatment. A plurality of the laser beams 7, 8 and 9 have perfectly the same optical axis or are within such a range as to cause practically no trouble, and irradiating position is not deviated even when the wavelength is changed.

Also, the laser beams 7, 8 and 9 may be irradiated at the same time from the first laser oscillator 4, the second laser oscillator 5, and the third laser oscillator 6 to synthesize different wavelengths of the laser beams. The following wavelengths may be used as the wavelengths of the laser beams 7, 8 and 9 irradiated from the first laser oscillator 4, the second laser oscillator 5, and the third laser oscillator 6 respectively: B: 450–500 nm; G: 500–560 nm; O: 560–610 nm; and R: 610–660 nm.

Figure 2:
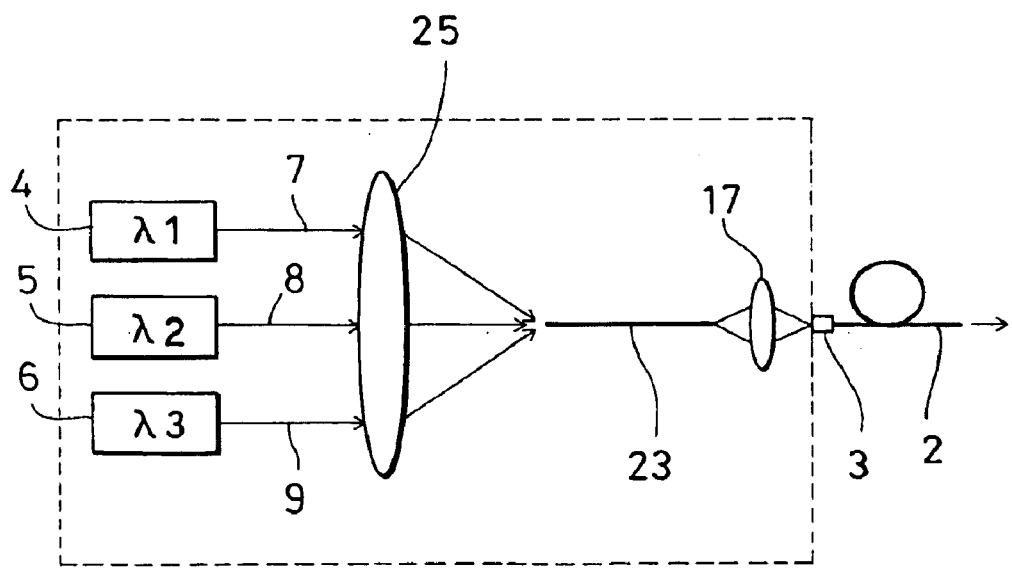
FIG. 2 is a schematical block diagram showing a second embodiment of the present invention.

FIG. 2 shows a second embodiment of the present invention. In FIG. 2, the same component as shown in FIG. 1 is referred by the same symbol, and detailed description is not given here.

In the second embodiment, a condenser lens 25 is used instead of the beam multiplexer 11 in the first embodiment, and, further, the second condenser lens 22 is not used.

In the second embodiment, the optical axis of each of the laser beams 7, 8 and 9 is made parallel to an optical axis of the condenser lens 25, and a converging point is aligned with an incident end surface of the beam mixing optical fiber 23.

Figure 3:
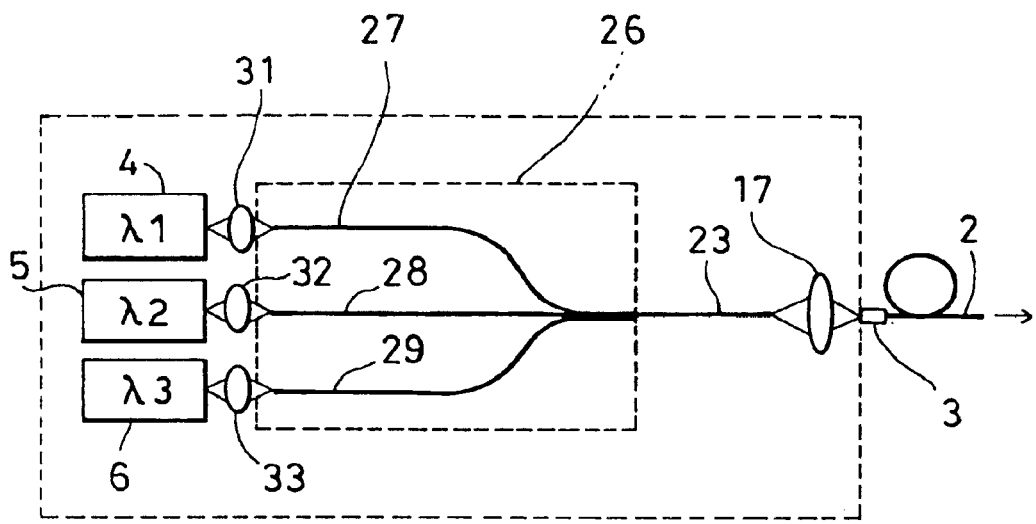
FIG. 3 is a schematical block diagram showing a third embodiment of the present invention.

FIG. 3 shows a third embodiment, in which a beam multiplexer 26 comprises optical fibers 27, 28 and 29.

In this embodiment, it is designed in such manner that a laser beam from the first laser oscillator 4 is converged to an incident end surface of the optical fiber 27 via a condenser lens 31, that a laser beam from the second laser oscillator 5 is converged to an incident end surface of the optical fiber 28 via a condenser lens 32, and that a laser beam from the third laser oscillator 6 is converged to an incident end surface of the optical fiber 29 via a condenser lens 33. The laser beams emitted from the first laser oscillator 4, the second laser oscillator 5, and the third laser oscillator 6 are superimposed on each other by the optical fibers 27, 28 and 29. Specifically, an exit end of each of the optical fibers 27, 28 and 29 is welded and deposited over a predetermined length. Then, the exit ends thus integrated by being welded and deposited are connected with the incident end of the beam mixing optical fiber 23.

Figure 4:
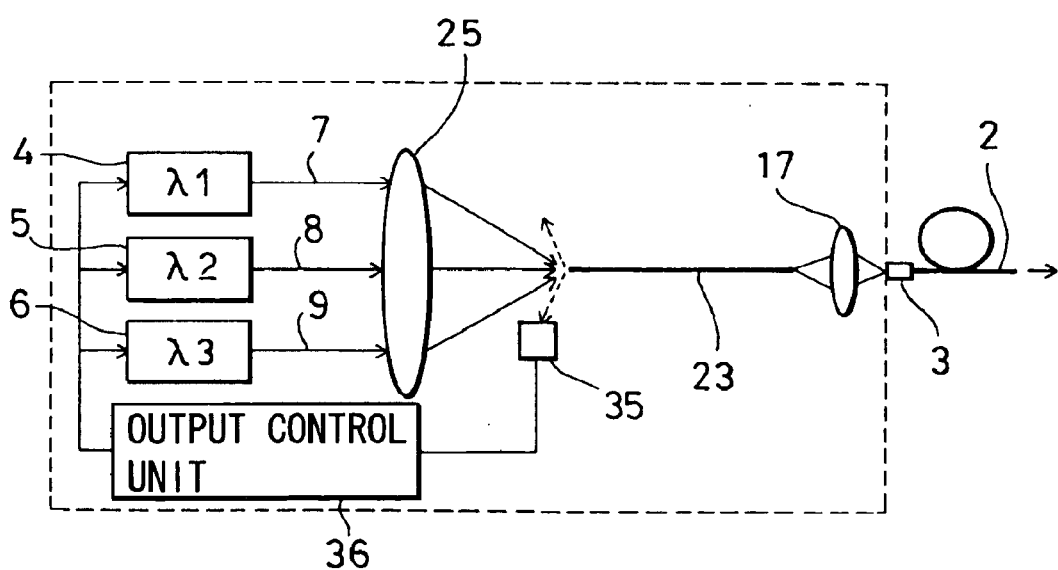
FIG. 4 is a schematical block diagram showing a fourth embodiment of the present invention.

In a fourth embodiment as shown in FIG. 4, exit intensity of each of the laser beams 7, 8 and 9 from the first laser oscillator 4, the second laser oscillator 5, and the third laser oscillator 6 is controlled.

A photodetector 35 is provided adjacent to the incident end surface of the beam mixing optical fiber 23. A detection signal from the photodetector 35 is feedbacked to an output control unit 36.

A reflection light (including scattered light) is detected by the photodetector 35 when the laser beams 7, 8 and 9 enter the beam mixing optical fiber 23. Based on the detection signal, output of each of the first laser oscillator 4, the second laser oscillator 5, and the third laser oscillator 6 is controlled.

In case output of each of the laser beams 7, 8 and 9 is individually adjusted, the laser beams 7, 8 and 9 are allowed to enter the beam mixing optical fiber 23 individually. Based on the detection signal of the photodetector 35 in this case, the first laser oscillator 4, the second laser oscillator 5 and the third laser oscillator 6 can be controlled corresponding to the laser beams respectively.

In the above, the beam mixing optical fiber 23 is used as a means for adjusting beam quality of the laser beams 7, 8 and 9, while an optical waveguide may be used.

Also, it may be designed in such manner that the laser light source unit 10 emits at least laser beams of blue, green, and red, and the laser device according to the present invention may be used as a light source for a laser display.

The present invention provides a laser device, which comprises at least a plurality of laser beam emitting sources, a laser beam multiplexing means for superimposing the laser beams emitted from the laser beam emitting sources, and a beam mixing means where the laser beams from the laser beam multiplexing means enter. As a result, a plurality of laser beams emitted from the laser device are superimposed on the same optical axis, and no speckle of light intensity distribution occurs at the irradiating point.

Also, the present invention provides a laser device, which comprises the laser beam emitting sources, the laser beam multiplexing means and the beam mixing means integrated with each other, and the device can be attached to or removed from a medical treatment system via an optical connector. As a result, laser beams under optimal conditions can be used in the medical treatment system in simple manner.

What is claimed is:

1. A laser device for medical treatment system, comprising at least a plurality of laser beam emitting sources, a laser beam multiplexing means for superimposing the laser beams emitted from said laser beam emitting sources, and a beam mixing means where the laser beams from said laser beam multiplexing means enter and which is an optical fiber for reflecting the laser beams by multireflection inside said optical fiber, and a condenser lens for focusing and entering the laser beams from said beam mixing means to a second optical fiber for propagation wherein said beam mixing means emits the laser beams so that the laser beam emitted from said laser device has a relation of $10 \leq M^2 \leq 22$, where $W \cdot \Theta = M^2 \lambda / \pi$, M is a parameter to express the quality of the laser beam W is a beam waste, $\Theta$ is a spreading angle, and $\lambda$ is a wavelength of the laser beam.

2. A laser device for medical treatment system according to claim 1, wherein said beam mixing means is an optical waveguide.

3. A laser device for medical treatment system according to claim 1, wherein said beam multiplexing means has a plurality of optical fibers where the laser beams enter individually, and said optical fibers have output ends integrated by being welded and deposited.

4. A laser device for medical treatment system according to claim 1, wherein the laser beam propagated in said optical fiber for propagation has the relation of $10 \leq M^2 \leq 22$.

5. A laser device for medical treatment system according to claim 1, wherein $K1 \leq K2$, wherein K1 is a product of the numerical aperture NA1 of said beam mixing means and a core diameter D1, and K2 is a product of numerical aperture NA2 of said optical fiber for propagation and a core diameter D2.

6. A laser device for medical treatment system according to claim 1, wherein said beam mixing means is an optical fiber designed in the form of a coil.

* * * * *